US008808331B2

(12) United States Patent
Harper

(10) Patent No.: US 8,808,331 B2
(45) Date of Patent: Aug. 19, 2014

(54) OFFSET VARIABLE ANGLE CONNECTION ASSEMBLY

(75) Inventor: Michael Harper, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 111 days.

(21) Appl. No.: 13/278,471

(22) Filed: Oct. 21, 2011

(65) Prior Publication Data
US 2012/0041492 A1 Feb. 16, 2012

Related U.S. Application Data

(63) Continuation of application No. 12/686,134, filed on Jan. 12, 2010, now Pat. No. 8,070,781.

(51) Int. Cl.
*A61B 17/70* (2006.01)

(52) U.S. Cl.
USPC .......................................... 606/264; 606/267

(58) Field of Classification Search
USPC ......... 606/60, 61, 65, 66, 246–279, 300–321; 439/157; 403/384–400
See application file for complete search history.

(56) References Cited

U.S. PATENT DOCUMENTS

| 5,643,263 | A | 7/1997 | Simonson |
| 5,885,285 | A | 3/1999 | Simonson |
| 5,947,967 | A | 9/1999 | Baker |
| 6,183,473 | B1 | 2/2001 | Ashman |
| 6,471,703 | B1 | 10/2002 | Ashman |
| 6,520,962 | B1 | 2/2003 | Taylor et al. |
| 6,562,038 | B1 | 5/2003 | Morrison |
| 7,261,715 | B2 | 8/2007 | Rezach et al. |
| 7,377,922 | B2 | 5/2008 | Baker |
| 7,575,587 | B2 | 8/2009 | Rezach et al. |
| 7,744,635 | B2 * | 6/2010 | Sweeney et al. ............... 606/264 |
| 2003/0176862 | A1 | 9/2003 | Taylor et al. |
| 2004/0092930 | A1 | 5/2004 | Petit et al. |
| 2004/0147928 | A1 | 7/2004 | Landry et al. |
| 2005/0234450 | A1 | 10/2005 | Baker |
| 2007/0156142 | A1 | 7/2007 | Rezach et al. |
| 2007/0162008 | A1 | 7/2007 | Cline, Jr. et al. |
| 2007/0173833 | A1 | 7/2007 | Butler et al. |
| 2007/0238335 | A1 | 10/2007 | Veldman et al. |
| 2007/0270810 | A1 | 11/2007 | Sanders |
| 2007/0293861 | A1 * | 12/2007 | Rezach et al. ................... 606/61 |
| 2008/0195122 | A1 | 8/2008 | Castellvi et al. |
| 2009/0076549 | A1 | 3/2009 | Lim et al. |
| 2009/0234391 | A1 | 9/2009 | Butler et al. |

OTHER PUBLICATIONS

ISR and Written Opinion from PCT/US2011/020910.
IPRP from PCT/US2011/020910.

* cited by examiner

*Primary Examiner* — Mary Hoffman
*Assistant Examiner* — Christina Negrellirodrigue

(57) ABSTRACT

In a preferred embodiment, the present invention provides an offset connection assembly that can be used to securely connect a spinal implant to a bone anchor. In particular, the present invention preferably provides a variable angle connection assembly that is able to securely connect the spinal implant to the anchors even when there is a variance in the angle and position of the anchors with respect to the spinal implant. Furthermore, in a preferred embodiment, the present invention provides a connection assembly that will not inadvertently lock the components of the connection assembly preventing the relative movement of the components.

18 Claims, 3 Drawing Sheets

OFFSET VARIABLE ANGLE CONNECTION ASSEMBLY

CROSS-REFERENCE TO RELATED APPLICATIONS

This application is a continuation application of U.S. patent application Ser. No. 12/686,134 filed on Jan. 12, 2010 now U.S. Pat. No. 8,070,781, which is incorporated by reference in its entirety herein.

FIELD OF THE INVENTION

The present invention relates generally to a connection assembly, and more particularly, to a variable angle spinal implant connection assembly.

BACKGROUND OF THE INVENTION

Spinal deformities, spinal injuries, and other spinal conditions may be treated with the use of spinal implants. Spinal implants are designed to support the spine and properly position the components of the spine. One such spinal implant includes an elongated rod and a plurality of bone anchors. The elongated rod is positioned to extend along one of more of the components of the spine and the bone anchors are attached to the spinal components at one end and secured to the elongated rod at the other end.

However, due to the anatomical structure of the patient, the spinal condition being treated, and, in some cases, surgeon preference, the bone anchors may be required to be positioned at various angles and distances from the elongated rod. As a result, it can be difficult to obtain a secure connection between the elongated rod and the bone anchors.

As such, there exists a need for a connection assembly that is able to securely connect an elongated rod to bone anchors despite a variance in the angle and position of the bone anchors with respect to the rod.

SUMMARY OF THE INVENTION

In a preferred embodiment, the present invention provides a connection assembly that can be used to securely connect a spinal implant to a bone anchor. In particular, the present invention preferably provides an offset variable angle connection assembly that is able to securely connect the spinal implant to the anchors even when there is a variance in the angle and position of the anchors with respect to the spinal implant. Additionally, in a preferred embodiment, the present invention provides for a medial locking offset bone anchor connection that allows for the preservation of adjacent anatomical structure, such as adjacent facets. Furthermore, in a preferred embodiment, the present invention provides a connection assembly that will not inadvertently lock the components of the connection assembly preventing the relative movement of the components.

In a preferred embodiment, the connection assembly comprises a housing member that has an aperture for receiving a portion of a spinal implant, an opening for receiving a securing member for securing the spinal implant and a channel for receiving a receiving member. The receiving member preferably has an aperture for receiving a portion of an anchor, a rim portion having at least one ridge, and a lumen. In addition, in a preferred embodiment, the receiving member is configured and dimensioned to be received in the channel of the housing member so that the receiving member is rotatably and translatably connected to the housing member. An interference member is preferably received in the lumen of the receiving member and is translatable in the lumen. In a preferred embodiment, an end of the interference member has an anchor contacting surface for locking the anchor in place.

In a preferred embodiment, the connection assembly further comprises an annular member that is positioned over the receiving member and received in the channel of the housing member. Preferably, a face of the annular member has at least one ridge and the at least one ridge on the rim portion of the receiving member faces the at least one ridge on the second face of the annular member. In a preferred embodiment, the ridges are configured and dimensioned to engage with each other to lock rotational movement of the housing member and the receiving member.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figures 1, 3:
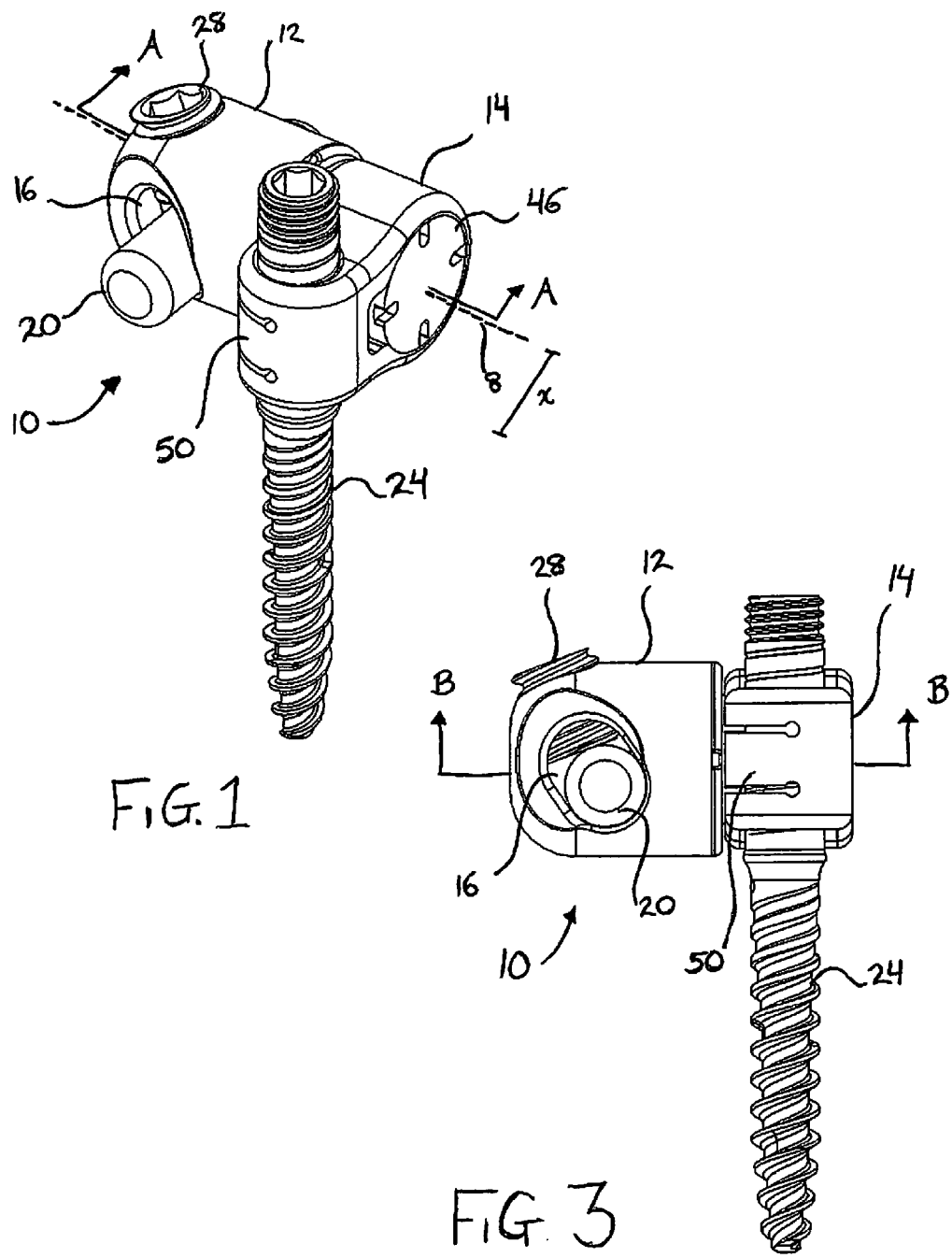
FIG. 1 is a perspective view of one embodiment of a connection assembly.
FIG. 3 is an elevated side view of the connection assembly shown in FIG. 1.

The following description of the preferred embodiment(s) is merely exemplary in nature and is in no way intended to limit the invention, its application, or uses.

With reference to FIGS. 1-4, a preferred embodiment of an offset connection assembly 10 is illustrated. The connection assembly 10 preferably includes a housing member 12 and an offset receiving member 14. The housing member 12 includes an elongated aperture 16 at a first end for receiving at least a portion of a spinal implant 20, such as a spinal rod, and the offset receiving member 14 includes an aperture 22 for receiving at least a portion of an anchor 24, such as a bone screw. The aperture 22 (and anchor 24) is linearly offset from the spinal implant 20, or in other words, the center of the aperture 22 is offset a distance x from a central axis 8. One of ordinary skill in the art would recognize that although only a bone screw is shown, the aperture 22 of the offset receiving member 14 is capable of receiving any number of anchors including, but not limited to, other orthopedic screws, hooks, bolts, or other similar bone anchoring devices. The housing member 12 and the offset receiving member 14 are preferably rotatably connected. The rotatable connection can be of any suitable design, including a threaded connection, a snap-fit, or a captured connection.

In a preferred embodiment, the housing member 12 also includes a second aperture 26 at the first end for receiving a securing member 28. The second aperture 26 extends from an outer surface of the housing member 12 toward the elongated aperture 16. In a preferred embodiment, the second aperture 26 is in fluid communication with the elongated aperture 16. At least a portion of the second aperture 26 is preferably threaded to receive the securing member 28, but the second aperture 26 can also be non-threaded.

Figure 2:
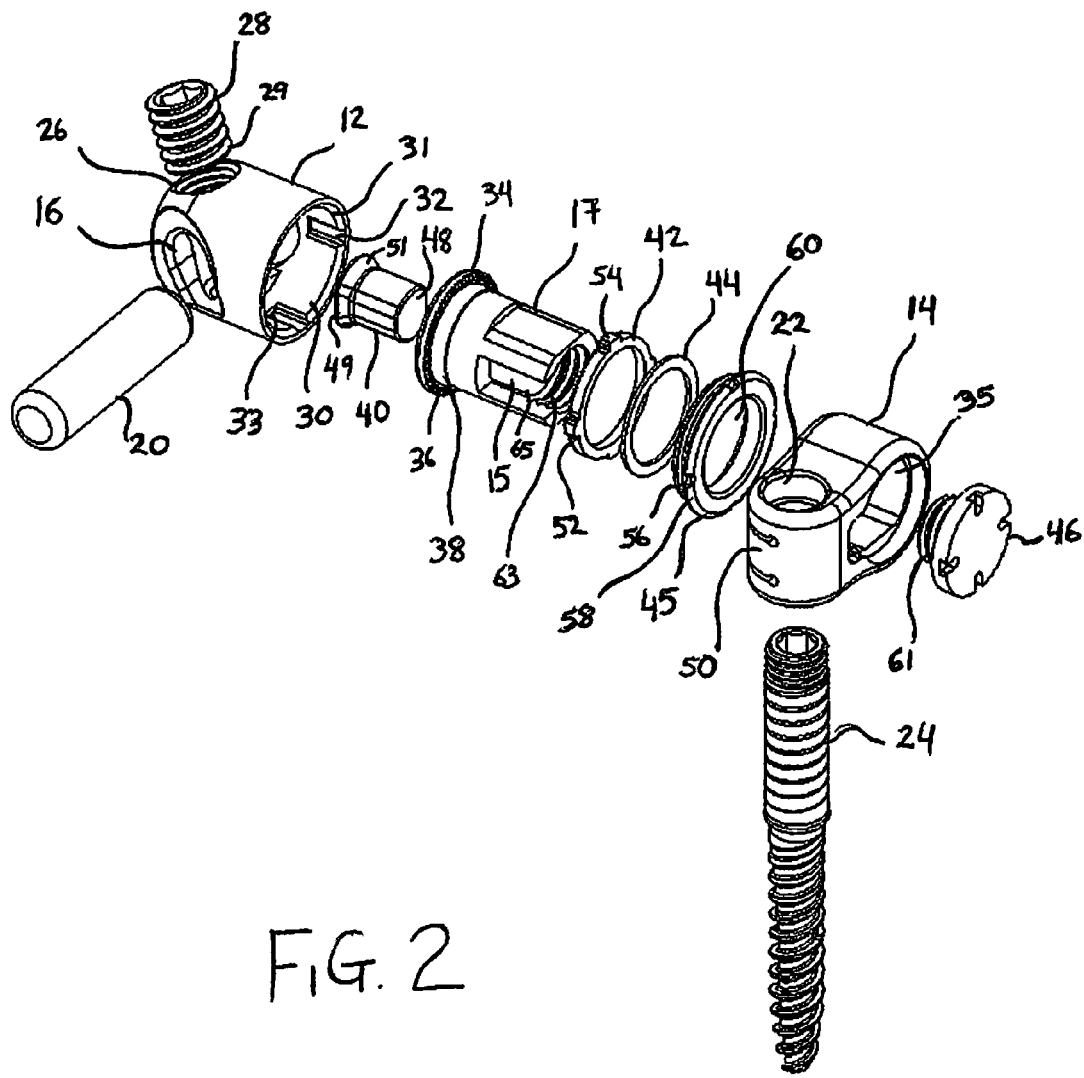
FIG. 2 is an exploded perspective view of the connection assembly shown in FIG. 1.

The securing member 28 is preferably a threaded set screw, as best seen in FIG. 2, but can be any type of securing member including, but not limited to, a bolt, a pin, a shoe, an interference member, or a cam member. In a preferred embodiment, the securing member 28 is captured in the second aperture 26 preventing accidental disengagement of the securing member 28 from the housing member 12. The securing member 28 is captured in the second aperture 26 by including an overhanging portion 29 on the securing member 28 that abuts against the termination of the threading in the second aperture 26.

With continued reference to FIG. 2, the housing member 12 also includes, in a preferred embodiment, a channel 30 which extends from a second end of the housing member 12 toward the first end of the housing member 12. The channel 30 is in fluid communication with the elongated opening 16. Preferably, at least a portion of the channel 30 includes threading 31 interrupted by at least one groove 32 extending from the second end of housing 12 toward the first end of housing member 12. In a preferred embodiment, the at least one groove 32 extends towards the first end of the housing member only a predetermined amount and preferably includes an end face 33 that defines the end of the groove 32.

Figure 5:
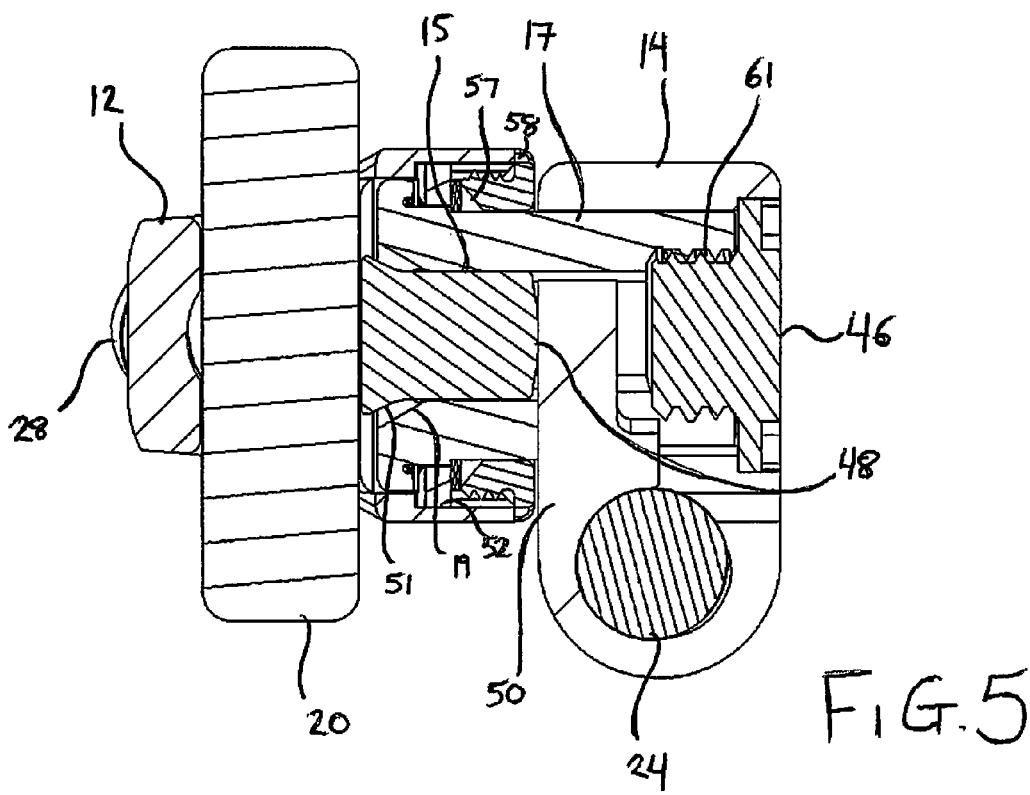
FIG. 5 is a cross-sectional view of the connection assembly shown in FIG. 1 in the direction of arrows B-B.

The offset receiving member 14, in a preferred embodiment, includes a first end and a second end, the aperture 22 located between the ends. The offset receiving member further includes a channel 35 and a resilient leg 50. Referring to FIGS. 2 and 5, the offset receiving member 14, in a preferred embodiment, receives in the channel 35 a connection member 17 which is generally cylindrical in shape with a generally cylindrical lumen 15.

The connection member 17 preferably includes threading 63 and a slot 65 at one end of the lumen 15, at a first end of the connection member 17. In another preferred embodiment, the lumen 15 may include a tapered shoulder portion 19. The connection member 17 further includes a radially outwardly extending rim portion 34 on a second end that has a plurality of ridges 36 preferably oriented toward the offset receiving member 14. In a preferred embodiment, the connection member 17 also has a shoulder portion 38, spaced from the rim portion 34, on the second end of the connection member 17. The connection member 17 is configured and dimensioned to be received within the channel 30 of the housing member 12 and be received within channel 35 of the offset receiving member 14.

Turning back to FIGS. 1-5, the offset connection assembly 10 further includes, in a preferred embodiment, an interference member 40, a gear 42, a ring member 44, a cap member 45 and an end cap member 46. The interference member 40 has a generally cylindrical shape that tapers, in part, from a second end to a first end. The taper forms a shoulder portion 51. In a preferred embodiment, the first end of the interference member 40 has an end portion 48 that is configured and dimensioned to abut a resilient leg 50 on offset receiving member 14. On a second end of the interference member 40, there is a face 49 which preferably is flat, but may also be arcuate and generally conforms to the shape of the spinal implant 20. In another preferred embodiment, the interference member 40 has a generally rectangular shape with a first end having an end portion 48 that is configured and dimensioned to abut the resilient leg 50 and a second end that flares outwardly and includes face 49 for abutting the spinal implant. The interference portion 40 is configured and dimensioned to be received within the lumen 15 of the connection member 17.

The gear 42, as best seen in FIG. 2, preferably is generally annular in shape and has a plurality of ridges 52 on one face and at least one projection 54 extending radially outwardly from the gear 42. In a preferred embodiment, the gear 42 is configured and dimensioned to fit over the shoulder portion 38 of the connection member 17 and within channel 30 of the housing member 12. The gear 42 is preferably oriented so that the ridges 52 face the ridges 36 on the rim portion 34 of the connection member 17 and the at least one projection 54 is received within the at least one groove 32 in the housing member 12.

Figure 4:
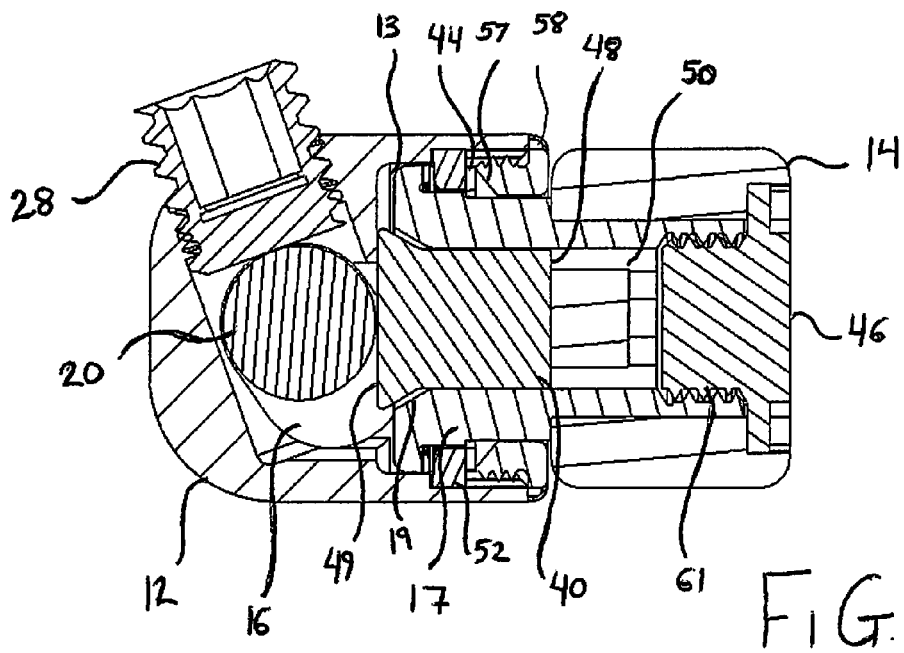
FIG. 4 is a cross-sectional view of the connection assembly shown in FIG. 1 in the direction of arrows A-A.

In a preferred embodiment, the ring member 44 is generally annular in shape, has a first face and a second face, and is configured and dimensioned to fit over the connection member 17 and abut against the shoulder portion 38, as best seen in FIGS. 4 and 5. Preferably, the ring member 44 also is configured and dimensioned to be received within the channel 30 of the housing member 12. In a preferred embodiment, the ring member 44 is made from titanium, but the ring member 44 can also be made from any biocompatible material including resilient polymers.

The cap member 45, in a preferred embodiment, is generally annular in shape and has a first face and a second face. The cap member 45 includes an extension portion 56 on the first face of the cap member 45 and a lumen 60. As best seen in FIGS. 2, 4 and 5, the extension portion 56 preferably is threaded along at least a portion thereof and includes a ramp portion 57. Although the extension portion 56 preferably includes threading, in another preferred embodiment, the extension portion may not be threaded. Preferably, the diameter of the extension portion 56 is smaller than the diameter of the portion of the cap member 45 immediately adjacent to the extension portion 56 creating a shoulder portion 58. In a preferred embodiment, the cap member 45 is configured and dimensioned so the extension portion 56 engages the threading 31 in the channel 30 of the housing member 12 and the shoulder portion 58 abuts the second end of the housing member 12. The lumen 60 of the cap member 45 is configured and dimensioned to receive the connection member 17. In a preferred embodiment, the cap member 45 is captured in the channel 30 of the housing member 12 to prevent the cap member 45 from inadvertently unthreading from the housing member 12.

The end cap member 46, in a preferred embodiment, is generally annular in shape and has a first face and a second face. The end cap member 46 includes an extension portion 61 on the first face of the end cap member 46. The extension portion 61 preferably is threaded along at least a portion thereof. Although the extension portion 61 preferably includes threading, in another preferred embodiment, the extension portion may not be threaded. In a preferred embodiment, the end cap member 46 is configured and dimensioned so the extension portion 61 engages the threading 63 in the lumen 15 of the connection member 17. As best seen in FIGS. 2, 4 and 5, at least a portion of the first face of the end cap member 46 abuts the second end of the offset receiving member 14. In a preferred embodiment, the end cap member 46 is captured in the lumen 15 of the connection member 17 to prevent the end cap member 46 from inadvertently unthreading from the connection member 17.

With reference to FIGS. 1 and 3-5, in a preferred arrangement of the elements of the offset connection assembly 10, the housing member 12 is rotatably connected to the offset receiving member 14. As mentioned above, the connection member 17 is received within the channel 30 of the housing member 12 and within the channel 35 of the offset receiving member 14. In a preferred embodiment, a second end of the connection member 17 abuts a medial wall 13 located within the housing member 12 and a first end of the connection member 17 extends beyond the second end of the housing member 12. Positioned within the lumen 15 of the connection member 17 is the interference member 40.

In a preferred embodiment, also received within the channel 30 of the housing member 12 is the gear 42 which fits over the shoulder portion 38 of the connection member 17. The at least one projection 54 on the gear 42 is received within the at least one groove 32 and preferably abuts the end face 33 of the groove 32. The end face 33 of the groove 32 is spaced from the medial wall 13 of the housing member 12 by a predetermined amount, so the gear 42, when placed in the channel 30, is spaced from the rim portion 34 of the offset receiving member 14 by a predetermined amount. Accordingly, the ridges 36 on the rim portion 34 are spaced from the ridges 52 on the gear 42. The purpose of this spacing is important and is explained further below.

In a preferred embodiment, the ring member 44 is also received within the channel 30 of the housing member 12 and also fits over the connection member 17. However, the inner diameter of the ring member 44 is smaller than the shoulder portion 38 of the receiving member 14. As a result, at least a portion of the second face of the ring member 44 will abut the shoulder portion 38. Preferably, the remaining portion of the second face of the ring member 44 will contact the gear 42.

The cap member 45, in a preferred embodiment, is also received within the channel 30 of the housing member 12 and also fits over the connection member 17. The threads on the threaded potion 56 engage with the threads 31 on the channel 30 to threadingly engage the cap member 46. Preferably, the threaded portion 56 is threaded into the channel 30 until the shoulder portion 58 contacts the second end of the housing member 12. In this position, the ramp portion 57 of the threaded portion 56 abuts the first face of the ring member 44.

The preferred arrangement of the elements, as discussed above, allow the housing member 12, the gear 42 and the cap member 45 to rotate with respect to the receiving member 14, the connection member 17, the ring member 44, the interference member 40, and the end cap member 46. As the housing member 12 rotates, the gear 42 will also rotate because of the at least one projection 54 located in the at least one groove 32. Likewise, since the cap member 45 is threaded and preferably captured in the channel 30 of the housing member 12, the cap member 45 also rotates when the housing member 12 rotates. In contrast, the connection member 17, although captured within the channel 30 of the housing member 12 by virtue of the cap member 45 and the rim portion 34, is capable of rotating as well as translating within the channel 30. Similarly, the ring member 44, although captured within the channel 30 of the housing member 12 by virtue of the shoulder portion 38 of the connection member 17 and the ramp portion 57 of the cap member 45, is capable of rotating within channel 30. Consequently, the ring member 44 does not rotate when the housing member 12 rotates. The receiving member 14 also is capable of rotating with respect to the housing member 12 as the receiving member 14 is connected to the housing member 12 through the connection member 17, which, as just discussed, is capable of rotating with respect to the housing member 12.

A preferred connection of the spinal implant 20 to the anchor 24 through the connection assembly 10 is best depicted in FIGS. 1, 2 and 3. In an exemplary use, the anchor 24 is implanted into a component of the spinal column, such as a vertebral body in the spinal column. Preferably, the aperture 22 of the receiving member 14 of the connection assembly 10 receives the anchor 24. The aperture 22 is configured and dimensioned to receive any portion of the anchor 24 allowing the connection assembly 10 to be placed anywhere along the length of the anchor 24. Accordingly, the connection assembly 10 can be translated along the anchor 24 until the desired position is achieved.

In an exemplary use, the spinal implant 20 is typically placed along at least a portion of the length of the spinal column in an orientation that is generally perpendicular to the anchor 24. Preferably, the spinal implant 20 is also received in the connection assembly 10, where the spinal implant 20 is received in the elongated opening 16 in the housing member 12. The elongated opening 16 is configured and dimensioned to receive any portion of the spinal implant 20 allowing the connection assembly 10 to be place anywhere along the length of the spinal implant 20.

Additionally, since the housing member 12 and the receiving member 14 are rotatably connected to each other, even if the anchor 24 and the spinal implant 20 are angularly offset, the connection member 10 can be oriented to a desired position to connect the spinal implant 20 and the anchor 24. Furthermore, as mentioned above, the anchor 24 is linearly offset from the spinal implant 20, or in other words, the anchor 24 is offset a distance x from the central axis 8, which is defined as extending from the first end of the housing member 12 to the second face of the end cap member 46. This linear offset allows for an offset connection of the anchor 24 to the spinal implant 20 thereby allowing for the preservation of adjacent anatomical components, such as the adjacent facets. Once the desired angular orientation and translational positioning of the connection assembly 10 with respect to the anchor 24 and the spinal implant 20 is achieved, the connection assembly 10 can be locked, securing the anchor 24 and the spinal implant 20.

To lock the connection assembly 10, the securing member 28 is threaded into the second aperture 26 in the housing member 12 where it contacts and pushes the spinal implant 20 toward the anchor 24. The spinal implant 20 contacts the face 49 of the interference member 40 and pushes the interference member 40 towards the anchor 24. As the interference member 40 is pushed by the spinal implant 20 towards the anchor 24, the interference member 40 moves in the lumen 15 of the connection member 17 towards the anchor 24, while the connection member 17 remains stationary. The end portion 48 of the interference member 40 abuts the resilient leg 50, pushing the resilient leg 50 into the anchor 24, which, in turn, pushes the anchor 24 into a sidewall of the aperture 22 in the receiving member 14, locking the anchor 24 in place with respect to the connector assembly 10.

As the spinal implant 20 continues to move towards the anchor 24 and continues to push the interference member 40, the shoulder portion 51 of interference member 40 abuts the walls of the lumen 15 and pushes against the walls of the lumen 15 moving the connecting member 17. As the connecting member 17 moves, the shoulder portion 38 pushes against the second face of the ring member 44. Since the first face of the ring member 44 abuts the ramp portion 57 of the cap member 46, after a predetermined force is applied to the ring member 44 by the shoulder portion 38, the ring member 44 deflects or bends in the direction of the ramp portion 57. With the ring member 44 no longer blocking the shoulder portion 38, the connecting member 17 continues moving towards the anchor 24 until the ridges 36 on the rim portion 34 of the receiving member 14 engage the ridges 52 on the gear 42. With the ridges 36 and 52 engaged, the relative rotation of the housing member 12 and the receiving member 14 of the connection assembly 10 is locked. At this point, the spinal implant 20 is also locked in place between the threaded member 28 and the walls of the housing member 12 that define the elongated opening 16. With the spinal implant 20 locked in place, the relative rotation of the housing member 12 and the receiving member 14 locked, and the anchor 24 locked in place, the entire assembly is locked against movement. Adjustments to the entire assembly can be made by loosening the threaded member 28 and then re-tightening the threaded member 28 once the preferred positioning and orientation has be achieved.

It is important to note that because of the shoulder portion 38 abutting the ring member 44 and the at least one projection 54 of the gear 42 abutting the end face 33 of the at least one groove 32, prior to the bending or deflection of the ring member 44, the ridges 36 on the rim portion 34 of the receiving member 14 can not engage the ridges 52 on the gear 42. This arrangement of elements prevents any inadvertent engagement of the ridges 36, 52 thereby preventing any unintended rotational locking of the housing member 12 with respect to the receiving member 14.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A connection assembly for connecting a spinal implant to an anchor, the connection assembly comprising:
   a housing member having a first end and a second end, the housing member having an aperture proximate the first end for receiving a portion of a spinal implant and a channel extending from the second end towards the first end, the channel is in fluid connection with the aperture and oriented generally transversely to the aperture;
   a connection member having a first end and a second end, the connection member having a lumen, the lumen is in fluid communication with the aperture of the housing member and oriented generally transversely to the aperture of the housing member, the second end of the connection member is received in the channel of the housing member so that the connection member is rotatably and translatably connected to the housing member;
   a receiving member having a first end and a second end, the receiving member having an aperture for receiving a portion of an anchor, a resilient leg for contacting an anchor, and a channel extending from the second end to the first end, the channel receives a first end of the connection member; and
   a cap member having a lumen and an extension portion, wherein the channel of the housing member receives the extension portion of the cap member.

2. The connection assembly of claim 1, the connection assembly further comprising:
   an annular member having a first face and a second face, the annular member positioned over the connection member and received in the channel of the housing member, wherein the connection member has a rim portion having at least one ridge proximate the second end, wherein the second face of the annular member has at least one ridge, and wherein the at least one ridge on the rim portion faces the at least one ridge on the second face of the annular member.

3. The connection assembly of claim 2, wherein the housing member has an opening proximate the first end for receiving a securing member.

4. The connection assembly of claim 3, further comprising a spinal implant in the aperture of the housing member, a bone anchor in the aperture of the receiving member, an interference member having a first end and a second end, the interference member received in the lumen and translatable in the lumen, the first end of the interference member having a resilient leg contacting surface, wherein the securing member presses the spinal implant against the interference member and the housing member to lock the spinal implant, the interference member, the connection member, the annular member and the bone anchor with respect to each other.

5. The connection assembly of claim 2, wherein the annular member has at least one projection and the channel has at least one groove for receiving the at least one projection.

6. The connection assembly of claim 1, the connection assembly further comprising a ring member having a first face and a second face, wherein the connection member has a shoulder portion, and wherein the ring member is positioned over the connection member and received in the channel, the second face of the ring member contacts the shoulder portion.

7. The connection assembly of claim 1, wherein the extension portion is threaded and at least a portion of the channel of the housing member is threaded so that the cap member is threadingly received in the channel of the housing member.

8. The connection assembly of claim 1, wherein the lumen of the cap member is configured and dimensioned to receive the connection member.

9. The connection assembly of claim 1, wherein the connection assembly has a central axis and the aperture of the receiving member is offset from the central axis.

10. A connection assembly for connecting a spinal implant to an anchor, the connection assembly comprising:
    a housing member having a first end and a second end, the housing member having an aperture proximate the first end for receiving a portion of a spinal implant and a channel extending from the second end towards the first end, the channel is in fluid connection with the aperture and oriented generally transversely to the aperture;
    a connection member having a first end and a second end, the connection member having a shoulder portion proximate the second end, and a rim portion proximate the second end, the second end of the connection member is received in the channel so that the connection member is rotatably and translatably connected to the housing member;
    a receiving member having a first end and a second end, the receiving member having an aperture for receiving a portion of an anchor and a channel extending from the second end to the first end, the channel receives a first end of the connection member;
    an annular member having a first face and a second face and at least one projection, the annular member positioned over the shoulder portion of the receiving member and received in the channel of the housing member; and
    a ring member having a first face and a second face, the ring member positioned over the receiving member and received in the channel of the housing member, the second face of the ring member contacting the shoulder portion.

11. The connection assembly of claim 10, further comprising:
    an interference member having a first end and a second end, the first end of the interference member having a contacting surface, the contacting surface configured and dimensioned to contact the resilient leg, wherein the connection member has a lumen extending from the second end towards the first end, the lumen is in fluid communication with the aperture of the housing member and oriented generally transversely to the aperture of the housing member, and wherein the interference member is translatably received in the lumen of the connection member.

12. The connection assembly of claim 11, wherein the connection assembly has a central axis and the aperture of the receiving member is offset from the central axis.

13. The connection assembly of claim 10, wherein the rim portion has at least one ridge, wherein the second face of the annular member has at least one ridge, and wherein the at least one ridge on the rim portion faces the at least one ridge on the second face of the annular member.

14. The connection assembly of claim 10, wherein the housing member has an opening proximate the first end for receiving a securing member.

15. The connection assembly of claim 14, further comprising a spinal implant in the aperture of the housing member, a securing member in the opening, and an anchor in the aperture of the receiving member, wherein the spinal implant is an elongate spinal rod, wherein the securing member is a set screw, and wherein the anchor is a bone screw.

16. The connection assembly of claim 10, wherein the extension portion is threaded and at least a portion of the channel of the housing member is threaded so that a cap member is threadingly received in the channel of the housing member.

17. A connection assembly for connecting a spinal implant to an anchor, the connection assembly comprising:

a housing member having a first end and a second end, the housing member having an aperture proximate the first end for receiving a portion of a spinal implant, an opening proximate the first end for receiving a securing member, and a channel extending from the second end towards the first end, the channel is in fluid connection with the aperture and oriented generally transversely to the aperture; and a connection member having a first end and a second end, the connection member having a shoulder portion proximate the second end, a rim portion proximate the second end, and a lumen extending from the second end towards the first end, the lumen is in fluid communication with the aperture of the housing member and oriented generally transversely to the aperture of the housing member, the second end of the connection member is received in the channel so that the connection member is rotatably and translatably connected to the housing member; and a receiving member having a first end and a second end, the receiving member having an aperture for receiving a portion of an anchor and a channel extending from the second end to the first end, the channel receives a first end of the connection member, wherein the connection assembly has a central axis and the aperture of the receiving member is offset from the central axis.

18. The connection assembly of claim 17, wherein the connection assembly has a central axis and the aperture of the connection member is offset from the central axis.

* * * * *